United States Patent [19]
Ward et al.

[11] Patent Number: 5,192,524
[45] Date of Patent: Mar. 9, 1993

[54] CAPTOPRIL AS A CANCER CHEMOPREVENTIVE AGENT

[75] Inventors: William F. Ward; Agostino Molteni, both of Evanston; Chung-hsin Ts'ao, Prospect Heights; Joann M. Hinz, Chicago, all of Ill.

[73] Assignee: Northwestern University, Evanston, Ill.

[21] Appl. No.: 514,589

[22] Filed: Apr. 26, 1990

[51] Int. Cl.$^5$ ................ A61K 43/00; A61K 31/40
[52] U.S. Cl. ................................... 424/1.1; 514/423
[58] Field of Search ................... 424/1.1; 514/423

[56] References Cited

PUBLICATIONS

CA 109(15): 125079h, Ward et al., *Int. J. Radiat. Oncol. Biol. Phys.*, 15(1), pp. 135-140 (1988).

*Primary Examiner*—Richard D. Lovering
*Assistant Examiner*—John M. Covert
*Attorney, Agent, or Firm*—Reising, Ethington, Barnard, Perry & Milton

[57] ABSTRACT

A method of inhibiting carcinogenesis following radiation therapy includes the steps of irradiating a tissue with x-ray or gamma radiation, administering Captopril after irradiation, reducing the severity of radiation induced normal tissue injury, and decreasing the risk of a secondary malignancy in the irradiated tissue.

4 Claims, 1 Drawing Sheet

CAPTOPRIL AS A CANCER CHEMOPREVENTIVE AGENT

This invention was made with Government support under Grant Number HL25106 awarded by the Government agency NIH. Government has certain rights in the invention.

TECHNICAL FIELD

The present invention relates to inhibitors of carcinogenesis, and more particularly, to the use of Captopril, previously used as an angiotensin converting enzyme inhibitor, to reduce the risk and incidence of radiation carcinogenesis.

BACKGROUND OF THE INVENTION

Radiation therapy is a common modality in the treatment of various malignancies. An untoward side effect of radiation therapy in the treatment of cancer or other disease states is the development of secondary cancers in the treatment area.

Captopril (Capoten, Bristol-Meyers Squibb, Princeton, N.J.) is an inhibitor of angiotensin converting enzyme. Clinically, Captopril has been used extensively in the management of systemic hypertension and congestive heart failure. Captopril was the first orally active inhibitor of angiotensin converting enzyme and is the subject matter of U.S. Pat. No. 4,046,889, issued Sept. 6, 1977 and assigned to Squibb Corporation.

Captopril has been found to have other biologically significant actions in addition to the ability of the drug to inhibit angiotensin converting enzyme. Presumably as a result of the sulphydryl group in its molecular structure, Captopril is a free radical scavenger (Chopra et al, Br. J. Clin. Pharmacol. 27 396-399 1989). Chopra et al suggested that this action may be relevant to the efficacy of the drug in heart failure and other vascular diseases (Chopra et al Br. J. Clin. Pharmacol. 27 396-399, 1989). Captopril has also been found to have antioxidant activity (Roberts and Robinson, Br. J. Rheumatol. 24 128-136 1985). This study was related to the identification of antirheumatic activity of the drug.

Captopril also may inhibit protease activity Kennedy et al. (in *Anticarcinogenesis and Radiation Protection*, ed. by P. A. Cerutti et al. Plenum Press, N.Y., 1987) reported on investigations of anticarcinogenic actions of various protease inhibitors. Proteases have been postulated to have various roles in cancer cells, and several protease inhibitors were found to be anticarcinogenic.

Besides the use of Captopril clinically in the management of systemic hypertension and congestive heart failure, (Franciosa, J. A. 1987 *Angiotensin Coverting Enzyme Inhibitors* ed. J. B. Kostis et al. Liss, N.Y., pp. 123-148; Gavras et al supra, pages 93-122), Captopril has been found to Hopewell, Br. J. Cancer, 53 (Suppl VII), 265-267, 1986), and to spare radiation induced pulmonary endothelial dysfunction in rats by the present inventors (Ward and Hinz, Prostaglandin and Lipid Metabolism in Radiation Injury, ed. by T. L. Walden et al, Plenum Press, N.Y., p. 147-158, 1987; Ward et al, Int. J. Radiat. Oncol. Biol. Phys, 15, 135-140, 1988). The results of further investigations of other angiotensin converting enzyme inhibitors as modifiers of pulmonary endothelial dysfunction and fibrosis caused by radiation have been published by the inventors (Ward et al, Radiat. Res. 117,342-350, 1989; Ward et al, Br. J. Radiol. 62,348-354 1989).

Although the aforementioned prior art discloses the use of Captopril in the management of systemic hypertension, congestive heart failure, pulmonary hypertension, diabetic renovascular disease, and rheumatoid arthritis, and the prior art further suggests various mechanisms of action of the drug, no prior art discloses or suggests the use of Captopril or like drugs as an anticarcinogenic agent.

Applicants have found that Captopril can be used in a method of reducing benign and malignant reactions, caused by x-ray or gamma radiation.

SUMMARY OF THE INVENTION

In accordance with the present invention, there is provided a method of inhibiting radiation induced carcinogenesis, the method including the steps of irradiating a tissue with x-ray or gamma radiation, administering Captopril after irradiation, reducing the severity of radiation induced normal tissue injury, and decreasing the risk of secondary malignancy in irradiated tissue.

FIGURES IN THE DRAWINGS

Other advantages of the present invention will be readily appreciated as the same becomes better understood by reference to the following detailed description when considered in connection with the accompanying drawings wherein:

FIG. 1 shows mean epilation score as a function of time (weeks) after irradiation in rats consuming either control diet (circles) or feed containing 0.08% (w/w) Captopril (triangles) continuously after irradiation. The SEM for all data points was +0.1, and was omitted for graphic clarity. Analysis of variance revealed that Captopril had no significant effect on epilation; and FIG. 2 shows incidence (%) of severe moist desquamation (score of 4.0=involving more than half of the radiation port) as a function of time (weeks) after exposure to 30 Gy of $^{60}$Co gamma rays in rats consuming either control diet (circles) or feed containing 0.08% (w/w) Captopril (triangles) continuously after irradiation.

DETAILED DESCRIPTION OF THE INVENTION

Figure 1:
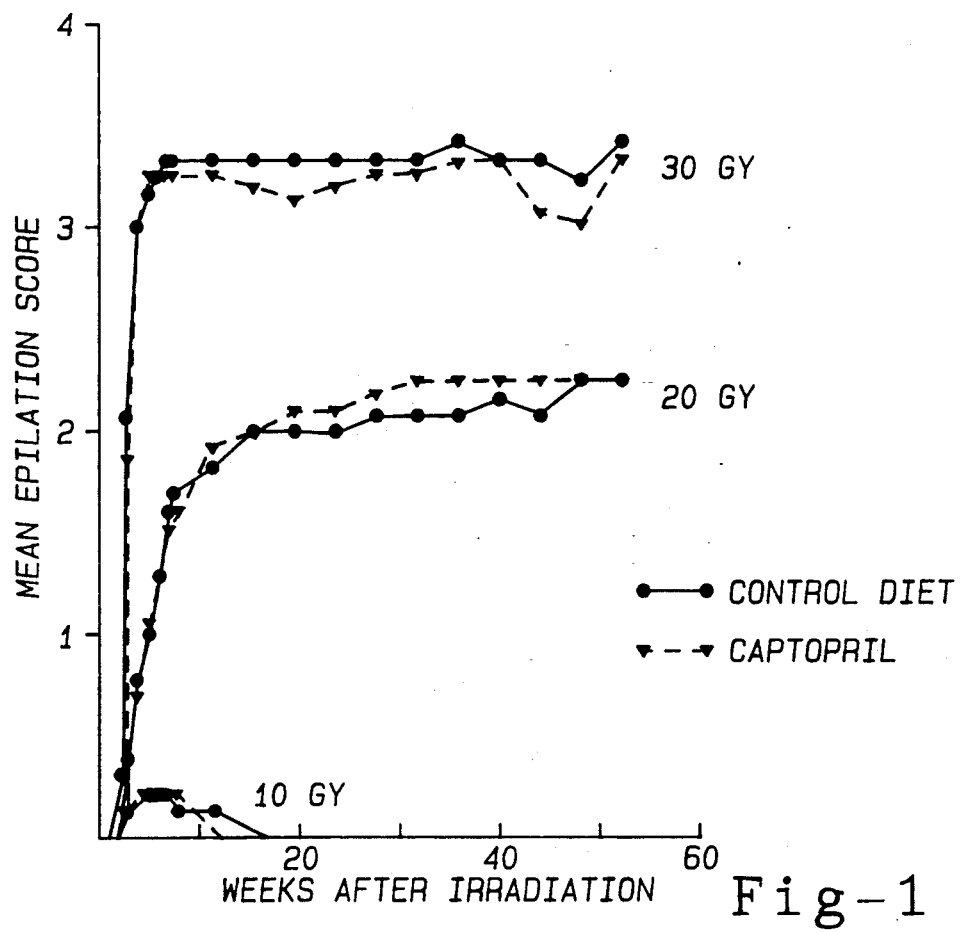

The present invention provides a method of protecting tissues from carcinogenesis. Specifically, the present invention provides a means of decreasing the risk and occurrence of tumor formation after radiation of tissue by x-ray or gamma radiation.

The effect of Captopril can be considered cancer chemopreventive. That is, Captopril reduces the incidence of secondary malignant tumors caused by radiation therapy. The mechanism of action is most likely effected at some as yet unidentified point(s) during the sequence from transformation to promotion to progression of the cancer. Captopril protects the tissue exposed to radiation from the development of secondary malignancies.

Generally, the method includes the steps of irradiating the tissue with x-ray or gamma radiation and administering Captopril after irradiation. Captopril can be administered immediately after radiation and continuously for an extended period of time due to the otherwise low toxicity and side effects caused by the administration of Captopril systemically.

Preferably, the present invention would be utilized in conjunction with radiation therapy, such as that used in the treatment of cancer.

Preferably, Captopril would be orally administered. Since oral administration of Captopril is very well characterized and issues such as bioavailability and toxicity are well characterized, oral administration is the preferable mode of administration.

The following data shows that the administration of Captopril continuously after irradiation reduces the severity of radiation induced normal tissue injury consistent with previous findings of Ward et al, as previously discussed (Ward et al 1987, 1988 supra). Unexpectedly, however post-radiation administration of Captopril also decreases the risk of secondary malignancy in the irradiated tissue.

EXPERIMENTAL EVIDENCE

Materials and Methods

Male Spraque-Dawley rats (Charles River, Boston, Mass.) were housed at 23°±1° C., and were given powdered chow (Ralston Purina, St. Louis, Mo.) and tap water ad libitum. The drinking water contained 500 mg of oxytetracycline (Sigma Chemical Co., St. Louis, Mo.) per liter in order to prevent outbreaks of respiratory infections. All animals were housed in and cared for by the staff of the AAALAC-accredited Northwestern University Center for Experimental Animal Resources, in accord with NIH guidelines on the humane use of warm-blooded animals in research.

Rats weighing 350–400 g were anesthetized with sodium pentobarbital (30 mg/kg, i.p.), and were exposed to single doses (10, 20, 30 Gy) of $^{60}$Co gamma rays to a 3.5 cm$^2$ right hemithorax port as described in Ward et al, 1987. The dose was approximately 2.0 Gy min$^{-1}$. A staggered stack of 8 mm-thick paraffin blocks was placed adjacent to the right thorax, in order to eliminate the air space between the block tray and the treatment table within the port. Comparably handled sham-irradiated rats served as controls. Half of each radiation dose group consumed control powdered chow, and half consumed chow containing 0.08% (w/w) Captopril (E. R. Squibb, Princeton, N.J.) continuously after irradiation. The control and experimental diets were available immediately after irradiation, although animals in neither group consumed much feed in the first 24 hours after anesthesia (irradiation). Food consumption was measured periodically, and remained fairly constant at 25±2 g/rat/day in all treatment groups throughout the study. This resulted in an average daily Captopril consumption of 20 mg per rat, a dose that was not adjusted for body weight gain. Thus the Captopril regimen decreased from 50 mg/kg/day to 25 mg/kg/day as the animals increased in body weight by a factor of approximately 2.0 during the 52-week study. Although this dosage is relatively higher when compared to prescribed therapeutic doses for humans, rats also require 10 times as much drug to relieve hypertension as do humans on an equivalent body weight basis.

Animals were observed daily for the presence of tumors. Body weight, epilation, and moist desquamation were recorded weekly for the first 8 weeks, then biweekly for 52 weeks after irradiation. All treatment groups consisted initially of 32 rats, with 8 animals per group scheduled for autopsy at 13, 26, 39, and 52 weeks after irradiation in order to evaluate pulmonary reactions.

Epilation in the port was scored on a scale of 0=none; 1.0=slight; 2.0=moderate; 3.0=severe; and 4.0=total, by two investigators unfamiliar with the treatment history of the animal. Moist desquamation was scored concurrently on a scale of 0=none; 1.0=skin surface intact but irregular; 2.0=one to a few scattered foci of desquamation; 3.0=confluent, but involving less than half of the port; and 4.0=involving more than half of the port. Tumor masses were fixed in 10% neutral buffered formalin at autopsy, sectioned at 6 um, stained with hematoxylin and eosin, number-coded, and evaluated by a veterinary pathologist.

All data were subjected to multiple analysis of variance, in order to assess the significance of the three controlled variables (time, radiation dose, and diet). Scores for epilation and moist desquamation were obtained at each observation time as the arithmetic mean from all members of the treatment group. The significance of differences between group means was determined by the Neuman-Keuls test. Tumor incidence was evaluated by Chisquare analysis (Zar, J. C., 1974, *Biostatistical Analysis*. Prentice Hall, Englewood Cliffs, N.J., pp. 121–181). All values represent the mean+-SEM.

RESULTS

Most of the rats consuming control diet became extremely obese after 6 months of ad libitum access to powdered food; several exceeded 900 g body weight by nine months. Captopril-treated rats consumed approximately 10% less food and gained approximately 15% less body weight than did control-fed animals throughout the study (data not shown). In all other respects, Captopril-treated animals were indistinguishable from controls. A total of seven animals were sacrificed in extremis from tumor growth or lung damage prior to their scheduled autopsy time, and two animals died prematurely of other causes. Of these nine cases, only two were Captopril-treated animals.

Epilation

Hair loss in the radiation port was minor and transient (3–12 weeks) after 10 Gy, but became increasingly severe and permanent with increasing radiation dose (FIG. 1). In animals exposed to 30 Gy, epilation appeared at two weeks postirradiation, reached a peak at seven weeks, then persisted essentially unchanged through 52 weeks. The severity of epilation in animals receiving Captopril was not significantly different from that in control animals at any radiation dose (FIG. 1).

Moist Desquamation

Figure 2:
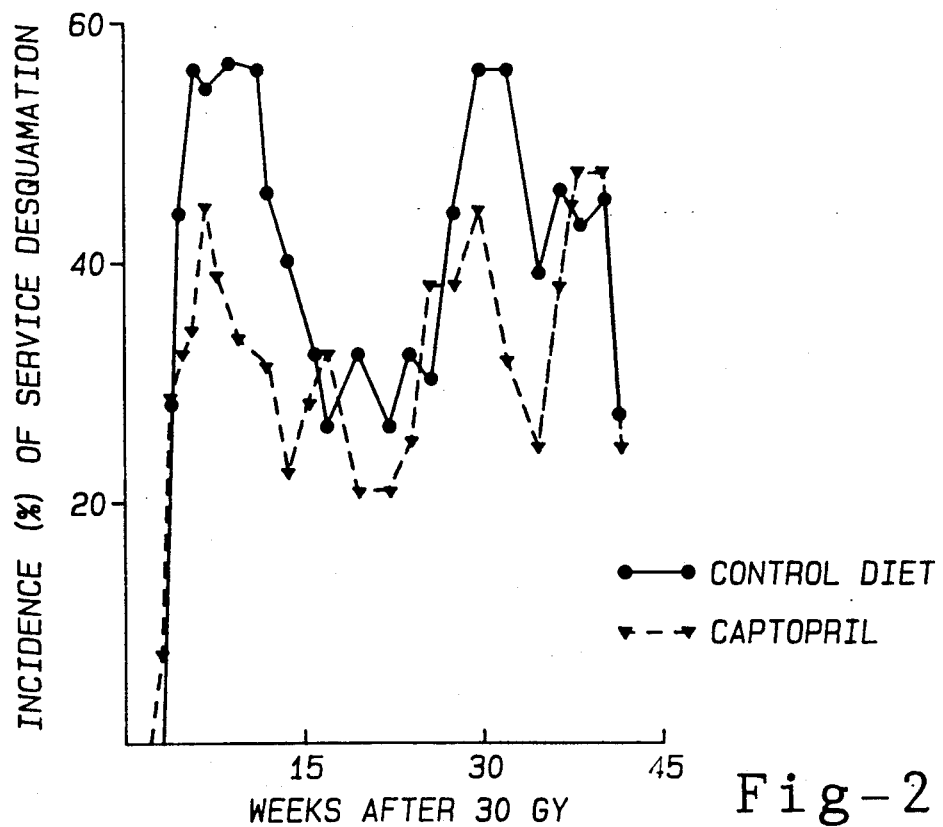

Moist desquamation was not observed after 0 or 10 Gy, and was rare after 20 Gy in both the control and Captopril-treated animals (Table I). In rats exposed to 30 Gy, however, two waves of moist desquamation were observed. The first wave occurred at three weeks postirradiation, reached a peak at 6–10 weeks, then resolved partially but significantly from 12 to 26 weeks postirradiation (Table I). The second wave of moist desquamation began at 26–28 weeks, reached a peak at 30–32 weeks, and then subsided irregularly through 52 weeks (Table I). The second wave of desquamation often was ulcerative and precipitous, occasionally exhibiting almost complete breakdown of a previously intact skin surface within a one-week period. Multiple analysis of variance revealed that the mean desquamation score after 30 Gy was significantly (p 0.05) lower in animals receiving Captopril than in the control animals (Table I). The biphasic nature of the moist desquamation reaction could be seen clearly when the incidence (%) of animals exhibiting the most severe reaction (4.0=involving more than half of the port) was plotted as a function of time after 30 Gy (FIG. 2). Captopril reduced the area under both waves by approximately one-third ($P<0.05$). Captopril did not influence the time of onset of either wave, rather it reduced the peak incidence and accelerated the resolution of both phases of the moist desquamation reaction (FIG. 2). As a result, Captopril-treated animals exhibited a third wave of severe desquamation at 38-40 weeks, which was masked in the control animals (FIG. 2).

Carcinogenesis

A total of 14 tumors was observed in the radiation ports of 11 rats during the study, and all were fibrosarcomas or squamous cell carcinomas (Table II). Most tumors were detected 36 weeks or longer after 30 Gy. Of the 14 tumors, only 3 ($Chi^2=4.57$, $p<0.05$) were detected in rats receiving Captopril. Multiple tumors (three cases), tumors induced by 20 Gy (three cases), and tumors appearing before 26 weeks (one case) were observed only in rats consuming control diet, never in Captopril-treated animals (Table II). Rats developing tumors in the second 6 months postirradiation exhibited significantly more severe moist desquamation during the first 6 months than did the tumor-free members of their treatment group (Table III).

DISCUSSION OF EXPERIMENTAL DATA

Consistent with the prior findings relating to Captopril in kidney (Robbins and Hopewell, Br. J. Cancer, 53 (Suppl. VII), 265-267, 1986) and lung (Ward et al 1987, 1988 supra), the above data demonstrates that Captopril also reduces radiation reactions in skin. It is further expected that the cancer chemoprotective effect of Captopril will be found with other thiol-containing angiotensin converting enzyme inhibitors.

The two waves of moist desquamation observed after 30 Gy shown by the data are a well documented response to high doses of radiation in several species. (Field, Radiology, 92, 381-384 1969; Hopewell, Br. J. Radiol., Suppl. 19, 39-47 1987). It has been proposed that the first wave results from epithelial damage and the second wave results from vasculo-connective tissue damage. The above data indicates a Captopril reduced both waves by approximately the same extent, that is, by one-third.

The mechanism of action of Captopril in the above tested models is not clear at present. Captopril is not only an angiotensin converting enzyme inhibitor but is also a thiol compound. The presence of the sulfhydryl moiety appears to account for some (but only some) of the drug's radiation modifying activity in lung. (Ward et al, 1989 supra.) It is expected that other angiotensin converting enzyme inhibitors containing thiols, such as CL242817 from Cyanamid Lederle, will have similar cancer chemo-protective effects.

Other agents are known to ameliorate skin damage when administered after irradiation. These agents include anti-inflammatory agents (Bjornberg et al, Treatment of radiation dermatitis with Fluocinolone acetonide. *Acta Radiological Therapy Physics Biology,* 3, 129-134 1965; Bielicky et al, Effect of chloroquinediphosphate administration on the skin damage in guinea pigs caused by x-ray irradiation, *Journal of Investigative Dermatology,* 47, 73-77, 1966; Chung et al, Effect of anti-inflammatory compounds on. β-irradiation induced radiodermatitis, *Dermatologica,* 44, 97-107, 1972), L-triiodothyronine (Glicksman, A. S. et al, Modification of late radiation injury with L-triiodothyronine. Radiology, 73, 178-190, 1959; Kitagawa, T. et al, Radiation effects on skin and subcutaneous tissue. A quantitative study of collagen content: modification with L-triiodothyronine. Radiation Research, 15, 761-766, 1966), and pentoxifylline (Dion et al, The effect of pentoxifylline on early and late radiation injury following fractionated irradiation in C3H mice, *International Journal of Radiation Oncology, Biology and Physics,* 17, 101-107, 1989). Moreover, anti-inflammatory agents have been shown to reduce the severity of radiation-induced skin ulcers without influencing epilation, as does Captopril (Chung et al supra). Captopril is not commonly regarded as an anti-inflammatory agent, although it does exhibit that action in patients with rheumatoid arthritis, (Martin et al, 1984, Captopril: a new treatment for rheumatoid arthritis? The Lancet, 1, 1325-1328, 1984).

The present invention does demonstrate for the first time that Captopril reduces the incidence of malignancies in the radiation treatment field. The mechanism of this anticarcinogenic action is not entirely understood, although tumorigenesis and severe desquamation may not be entirely independent events. All animals which develop tumors during the second six months exhibited severe desquamation during the first wave of skin reaction at 6 to 10 weeks post-irradiation. It is possible that by reducing the frequency of severe early desquamation, Captopril reduced the pool of animals at risk and thereby indirectly decreased the incidence of tumors.

As a thiol, however, it is possible that Captopril exhibited a more direct anticarcinogenic action. Thiols such as cysteamine protect against carcinogenesis when given prior to irradiation. Milas et al 1984, Inhibition of radiation carcinogenesis in mice by S-2-(3-aminopropyl amino)ethylphosphorothioic acid, *Cancer Research,* 44, 5567-5569. In accordance with the present invention, however Captopril is given only after irradiation.

The thiol WR1065 reduces mutagenesis when given after irradiation (Grdina et al, 1985, The radioprotector WR1065 reduces radiation-induced mutations at the hypoxanthine-guanine phosphoribosyl transferase locus in V79 cells, Carcinogenesis, 6, 929-931), although the longest post radiation time interval tested in the Grdina et al study was 3 hours.

As stated above, Captopril is known to be a radical scavenger and to form copper complexes possessing antioxidant activity. These molecular mechanisms might reduce chronic events in radiation pathophysiology and carcinogenesis. As an inhibitor of a peptidase, Captopril may also exhibit some of the properties of protease inhibitors. That property most relevant to the present discussion is the suppressive effect of protease inhibitors on radiation carcinogenesis in vitro (Kennedy et al Antipain, but not cycloheximide, suppresses radiation transformation when present for only one day at five days postirradiation, *Carcinogenesis,* 3, 1093-1095, 1982; Kennedy et al, Anticarcinogenic action of protease inhibitors, in *Anticarcinogenesis and Radiation Protection,* Ed. by P. A. Cerutti, O. F. Nygaard, & M. G. Simic (Plenum, N.Y.), 285-295, 1987; Kennedy et al, Protease inhibitors suppress radiation induced malignant transformation in vitro, *Nature* (London), 276 825-826, 1978), and on chemical carcinogenesis in vivo. (Weed et al, Protection against dimethylhydrazine induced adenomatous tumors of the mouse colon by the dietary addition of an extract of soybeans containing the Bowman-Birk protease inhibitor, *Carcinogenesis*, 6, 1239-1241, 1985; Messadi et al, Inhibition of oral carcinogenesis by a protease inhibitor, *J. N. C. I*, 76 4476-452, 1986). Kennedy has shown protease inhibitors to be anticarcinogenic even when administered after radiation. (Kennedy et al, 1982 supra).

The rat model tested and discussed herein is an excellent predictive and relevant model to humans. Captopril has shown similar biological actions in rats and humans in various systems tested, such as in antihypertensive activity, inhibition of platelet aggregation, stimulation of interleukin-2 production and renal blood flow. Migdalof, B. H. et al, 1984, Drug Metab. Rev. 15, 841-869. The drug has been shown to be effective in these functions in rats and humans by having oral action, a similar route of excretion, and similar plasma levels. Accordingly, the drug has similar pharmacodynamics in both rats and humans.

It is possible that Captopril can be used to protect against carcinogenesis induced by other chemical oxidizers (e.g. some cancer chemotherapy drugs) as well as against radiation oxidation. In other words, it is possible that Captopril could have a protective effect against carcinogenesis caused by other cancer chemotherapeutic drugs. This could certainly increase the scope of use of these drugs by decreasing a critical toxicity caused thereby.

It is further possible other angiotensin converting enzyme inhibitors, particularly those containing a thiol moiety, could have a protective effect against carcinogenesis.

What is claimed is:

1. A method of protecting against carcinogenesis induced by radiation therapy, said method including the steps of: irradiating a tissue with X-ray or gamma radiation; administering Captopril after irradiation in an amount effective for reducing the severity radiation induced normal tissue injury and decreasing the incidence of a secondary malignancy in the irradiated tissue.

2. A method as set forth in claim 1 wherein said administering step is further defined as administering the Captopril in the effective amount continuously after irradiation for a predetermined period of time.

3. A method as set forth in claim 1 wherein said irradiation step is further defined as irradiating any tissue which is contacted by the Captopril.

4. A method as set forth in claim 1 wherein said administering step is further defined as orally administering the Captopril.

* * * * *